United States Patent [19]
Kreienbühl et al.

[11] Patent Number: 6,150,561
[45] Date of Patent: Nov. 21, 2000

[54] METHOD OF MAKING CAROTENOIDS

[75] Inventors: Paul Kreienbühl, Riehen; Peter Rudin, Basel; Werner Rudolph, Riehen, all of Switzerland

[73] Assignee: Roche Vitamins Inc., Parsippany, N.J.

[21] Appl. No.: 09/148,088

[22] Filed: Sep. 4, 1998

[30] Foreign Application Priority Data

Oct. 3, 1997 [EP] European Pat. Off. .............. 97117192

[51] Int. Cl.⁷ .................................................... C07C 45/00
[52] U.S. Cl. .......................... 568/352; 568/343; 568/345; 568/347; 568/348
[58] Field of Search ..................................... 568/343, 345, 568/347, 348, 352

[56] References Cited

U.S. PATENT DOCUMENTS

| | | | |
|---|---|---|---|
| 3,496,170 | 2/1970 | Chechak et al. | 260/240 |
| 3,517,067 | 6/1970 | Stern et al. | 260/606.5 |
| 5,654,488 | 8/1997 | Krause et al. | 568/365 |

FOREIGN PATENT DOCUMENTS

| | | |
|---|---|---|
| 0 733 619 | 9/1996 | European Pat. Off. . |
| 195 09 955 | 9/1996 | Germany . |

OTHER PUBLICATIONS

Mayer et al., "Carotenoids", p. 370, published by Birkhauser Basel (1971).

*Primary Examiner*—Sreeni Padmanabhan
*Attorney, Agent, or Firm*—Mark E. Waddell; Stephen M. Haracz; Bryan Cave LLP

[57] ABSTRACT

A widely applicable process for the manufacture of carotenoids by a Wittig reaction comprises carrying out the Wittig reaction in a polar reaction medium in a manner such that neither the reactants nor the thus-manufactured carotenoid are significantly dissolved in the reaction medium. An especially suitable reaction medium is a polar, toxicologically harmless solvent which remains monophasic on the addition of water in an amount up to about 30 vol. % and which permits the triarylphosphine oxide which is formed to dissolve well. Lower alcohols and acetone, as sole solvents or as mixtures with one another and/or with water, are especially suitable as the polar reaction medium. This process permits the use of much more concentrated reaction mixtures, simplifies the regeneration of the solvent and generally the reaction procedure, and avoids toxicologically objectionable solvents such as halogenated hydrocarbons.

29 Claims, No Drawings

METHOD OF MAKING CAROTENOIDS

BACKGROUND OF THE INVENTION

Carotenoids are a class of substances widely distributed in nature and having very interesting properties. Accordingly, there is great interest in industrially realizable syntheses. The Wittig reaction plays a very important rôle in the formation of the carotenoid polyene chain. It has been investigated extensively and also used industrially.

Carotenoids (intermediates and final products), e.g., carotenes and xanthophylls, are in the normally desired (all E) configuration poorly soluble in most solvents. Aromatic hydrocarbons and especially halogenated, lower aliphatic hydrocarbons, such as chloroform and methylene chloride, occupy as solvents a certain special position because of their good ability to dissolve carotenoids, and have hitherto preferably been used for this purpose. However, at present the dwindling acceptance of such solvents is disadvantageous for known and justified reasons. In addition, carotenoids have a typical property of incorporating solvents in non-stoichiometric amounts. Residues of the aforementioned solvents are subject to strict regulations, which, moreover, are not the same everywhere. The thermal stability of carotenoids is, however, frequently critical and therefore the removal of the incorporated traces of solvent is difficult and generally can be realized only at the expense of the commencement of decomposition.

The known industrial processes can be divided into the following sub-groups:

1) Homogeneous processes, in which the educts and the product remain in solution during the entire reaction; the isolation of the end product is carried out by precipitation, typically associated with an isomerization step.
2) Two-phase processes, in which the educts are dissolved in an organic solvent to which the required base is added, but in aqueous solution. For the working up, the phases are separated from one another and the organic phase is worked up similarly as in 1).
3) Heterogeneous processes, in which the educts are used in undissolved form. However, a clear solution results at least temporarily during the reaction. On the other hand, there are also reverse embodiments in which the reaction is started as a solution and the product precipitates during or after the actual reaction.

The Wittig reaction, which involves the reaction of a carbonyl compound such as an aldehyde or ketone with a triphenylphosphine compound known as a ylide, is generally carried out under basic conditions or at least in the presence of an acid-binding substance. As a waste product of the Wittig reaction there always results one equivalent of triphenylphosphine oxide, which has to be separated from the reaction mixture. The choice of solvent has a decisive influence on the working up.

The most important side reaction which generally occurs in the case of a Wittig reaction is the hydrolysis of the phosphonium salt: see the following Reaction Scheme.

Reaction Scheme

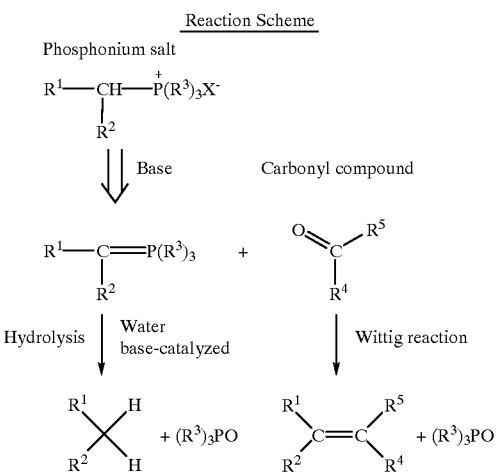

In this Scheme $R^1$ and $R^2$ and, respectively, $R^4$ and $R^5$ each signify hydrogen or an optionally substituted alkyl, alkenyl or aryl, e.g. phenyl, group, whereby a maximum of one of the two symbols $R^1$ and $R^2$ and, respectively, $R^4$ and $R^5$ can stand for hydrogen; $R^3$ signifies aryl, preferably phenyl, and X− signifies an anion, for example chloride, bromide, sulphate or acetate. Because of the preference of $R^3$, $(R^3)_3PO$ preferably signifies triphenylphosphine oxide. The carbonyl compounds are preferably aldehydes (which includes dialdehydes) and ketones, especially aldehydes, well known to a person skilled in the field of carotenoid chemistry. 2,7-Dimethyl-2,4,6-octatriene-1,8-dial ("$C_{10}$-dial") is an example of a typically used dialdehyde. Under "phosphonium salt" there is likewise to be understood especially one which is typically used for the synthesis of carotenoids and therefore will be well-known to a person skilled in the art. Many examples of pertinent Wittig reactions are contained in the textbooks "Carotenoids", Ed. Otto Isler, published by Birkhäuser Basel, 1971, and "Carotenoids, Volume 2: Synthesis", Ed. G. Britton, S. Liaaen-Jensen and H. Pfander, published by Birkhäuser Basel Boston Berlin, 1996.

The strength of base, the water content and/or the reaction temperature can be varied in a very broad range, in each case depending on the substrate, in order to avoid the side reaction which is mentioned above and set forth in the Scheme. Thus, it is known to carry out Wittig reactions in water as the solvent, whereas in other cases the reaction has to be carried out strictly water-free. The hydrolysis becomes relatively more rapid with increasing base strength and/or temperature, and accordingly temperatures of −30° C. to room temperature are frequently preferred; on the other hand there are cases in which a higher temperature is advantageously used. Furthermore, depending on the substrate, isomerization reactions of carotenoids are typical at higher temperatures.

The Wittig reaction can be carried out in practically all non-acidic solvents. Even acetone, which itself can react with phosphonium salts, has occasionally been used with success.

The aforementioned known embodiments of the Wittig reaction have disadvantages. The most preferred solvents from the toxicological point of view are water, lower alkanols, acetone and esters of acetic acid and other organic acids. These solvents, of which the organic solvents can be optionally combined with water, have as a rule only a very unsatisfactory ability to dissolve carotenoids. Thus, the heterogeneous reaction procedure is frequently used. An actual example of this is present in European Patent Publication (EP) 0733619. The limitations are especially apparent in this EP. In order to achieve a practicable concentration of educts with methanol or ethanol, both components must previously be dissolved while warming and (as an artifice) one educt must be used as an isomer mixture. The actual Wittig reaction requires in this example lower temperatures, and thus the reaction mixture must then be cooled down.

SUMMARY OF THE INVENTION

The object of the present invention is a chemically and industrially widely applicable process which enables carotenoids (not only intermediates but also final products) of widely differing structures to be manufactured while avoiding the aforementioned problems. This process comprises carrying out a Wittig reaction used for the manufacture of a carotenoid in a polar reaction medium in such a manner that neither the reactants nor the thus-manufactured carotenoid are significantly dissolved in the reaction medium.

DETAILED DESCRIPTION OF THE INVENTION

The invention comprises a method of making a carotenoid intermediate or carotenoid by reacting a dispersion of a carbonyl compound and a triphenylphosphonium salt in a polar reaction medium to obtain a dispersion of the resulting carotenoid intermediate or carotenoid and a solution of triphenylphosphine oxide. As used herein, "dispersion" includes slurries and non-colloidal suspensions.

As the respective polar reaction medium there is especially suitable a polar, toxicologically acceptable organic solvent which remains monophasic on addition of water in an amount up to about 30 vol. % and which has the capacity of dissolving well the triarylphosphine oxide which is formed. Especially suitable for this purpose are lower alkanols and acetone, which can be used individually or as a mixture with one another and/or with water. When these especially suitable polar solvents are used, additional polar solvents can, moreover, also be used. As such there come into consideration, for example, polar esters, especially the methyl and ethyl esters of formic acid, acetic acid or carbonic acid, methyl ethyl ketone, tert.butyl methyl ether and dimethylformamide. These additional polar solvents too can be used as mixtures with one another. In any event a reaction medium consisting of several of the aforementioned polar solvents should be monophasic (homogeneous).

The process in accordance with the invention is carried out in such a manner that neither the reactants, i.e., the respective carbonyl compound and the respective phosphonium salt, nor the thus-manufactured carotenoid are significantly dissolved in the reaction medium, whereas the triarylphosphine oxide, especially triphenylphosphine oxide, which is formed in the reaction medium remains in solution. Surprisingly good yields and end product quality can be achieved as a result of the process carried out in this manner.

In the scope of the above-defined process in accordance with the invention the term "neither the reactants—nor the thus-manufactured carotenoid are significantly dissolved" is to be understood as meaning that in the process a clear solution is not present at any time during the reaction and the working up, including the purification. The educts, an intermediate which may occur and the desired end product are present as a visually observed suspension or slurry, i.e., a dispersion. Depending on the reactant or product a maximum of 10% of its weight is present in solution. Typically, this degree of dissolution amounts to only between about 0.5 and about 2 weight percent. In certain cases this can even be much lower than 0.5 weight percent.

Further, under the term "alkanol" there is to be understood an alkanol which has 1 to 6 carbon atoms, especially 1 to 4 carbon atoms; examples thereof are methanol, ethanol, n-propanol and isopropanol. In the scope of the present invention a mixture of several of such alkanols with one another or a mixture of one or more of such alkanols with acetone can feature any desired number of these polar solvents and any desired mixture ratio. If water is also present (in the case of aqueous mixtures of one or more lower alkanols and/or of acetone) the mixture ratio among the mentioned polar organic solvents can be varied as desired. In the latter case the amount by volume of water relative to the total volume of the aqueous-organic solvents is normally not more than about 30%, preferably up to 20%. The methyl or ethyl ester of carbonic acid is dimethyl carbonate or diethyl carbonate, respectively. Methanol, ethanol, n-propanol and isopropanol are preferred among all the polar solvents which come into consideration.

The process in accordance with the invention functions not only for simple (one step) Wittig reactions, but even when two equivalents of a phosphonium salt are reacted with a symmetrical dialdehyde in one step without isolation of the intermediate. This procedure is denoted herein as a "double Wittig reaction".

The reaction should be run under conditions of temperature, time and concentration of reactants such that the reaction mixture is always in the form of a dispersion due to the insoluble reactants, intermediates or products present in the polar reaction medium. Such conditions may be any conventional conditions under which Wittig reactions are carried out except that dissolution of the reactants, intermediates or final products are less than about 10% by weight dissolved in the reaction medium, and the triphenylphosphine oxide byproduct of the Wittig reaction is in solution. These conditions will vary considerably due to the nature of the reactants and the final products, but may be monitored routinely by visual observation of the reaction.

In other respects the normal reaction conditions under which Wittig reactions are carried out apply, namely with respect to reaction temperatures, pressures, duration etc. Furthermore, the working up of the mixture obtained after completion of the reaction in order to isolate the product, and the purification of the product which may be carried out if desired, require only conventional measures. Although the invention is described with reference to triphenylphosphonium salts, any triarylphosphonium salts useful for carrying out a Wittig reaction to produce a carotenoid intermediate or carotenoid may be used in accordance with the present invention.

The process in accordance with the invention is suitable in principle for all Wittig reactions for the manufacture of carotenoids. The preferred reactions are as follows:

Zeaxanthin starting from [5-(4-hydroxy-2,6,6-trimethyl-1-cyclohexenyl)-3-methyl-2,4-pentadienyl] triphenylphosphonium chloride and 2,7-dimethyl-2,4,6-octatriene-1,8-dial ($C_{10}$-dial);

lycopene starting from [3,7,11-trimethyl-dodecyl-2,4,6,10-tetraenyl]-triphenylphosphonium chloride or acetate, especially the (2 E/Z, 4E, 6E,Z) isomer, and $C_{10}$-dial;

carotene starting from [3-methyl-5-(2,6,6-trimethyl-1-cyclohexenyl)-2,4-pentadienyl]triphenylphosphonium chloride, especially the (2E,4E) isomer, and $C_{10}$-dial;

canthaxanthin starting from [5-(2,6,6-trimethyl-3-oxo-1-cyclohexenyl)-3-methyl-2,4-pentadienyl] triphenylphosphonium chloride and $C_{10}$-dial;

astaxanthin starting from [5-(4-hydroxy-2,6,6-trimethyl-3-oxo-1-cyclohexenyl)-3-methyl-2,4-pentadienyl] triphenylphosphonium bromide, especially the (2E,4E) isomer, and $C_{10}$-dial;

crocetin diethyl ester starting from [3-ethoxycarbonyl-but-2-enyl]triphenylphosphonium chloride and/or bromide, especially the (E) isomer, and $C_{10}$-dial;

3-hydroxy-8'-apo-β-caroten-8'-oic acid ethyl ester starting from 3-hydroxy-12'-apo-β-caroten-12'-al, especially the (R)-isomer, and [3-ethoxycarbonyl-but-2-enyl]triphenylphosphonium chloride, especially the (E) isomer;

β-apo-4'-carotenal starting from the dimethyl acetal of [3-formyl-but-2-enyl]triphenylphosphonium chloride, especially the (E) isomer, and β-apo-8'-carotenal;

torularhodin aldehyde starting from the dimethyl acetal of [3-formyl-2-butenyl]triphenylphosphonium chloride, especially the (E) isomer, and β-apo-4'-carotenal;

diapo-4,4'-carotenedial starting from the dimethyl acetal of [7-formyl-3,7-dimethyl-octa-2,4,6-trienyl] triphenylphosphonium chloride and $C_{10}$-dial;

β-apo-8'-carotenoic acid ethyl ester starting from β-apo-10'-carotenal and (1-ethoxycarbonylethyl) triphenylphosphonium bromide;

β-apo-8'-carotenoic acid ethyl ester starting from β-apo-12'-carotenal and [3-ethoxycarbonyl-but-2-enyl] triphenylphosphonium chloride, especially the (E) isomer;

torularhodin starting from β-apo-8'-carotenal and [7-ethoxycarbonyl-3,7-dimethyl-2,4,6-heptatrienyl] triphenylphosphonium chloride via torularhodin ethyl ester;

as well as neurosporaxanthin ethyl ester (β-apo-4'-carotenoic acid ethyl ester) starting from β-apo-12'-carotenal and [7-ethoxycarbonyl-3,7-dimethyl-2,4,6-heptatrienyl]triphenylphosphonium chloride.

The process in accordance with the invention has great, practical advantages:

It is now possible to work with much more concentrated reaction mixtures (less solvent needed than used previously); the concentration is limited only by the reduced ability to stir. Thereby, space/time yields are substantially improved. Moreover, the regeneration of the solvent is simplified, especially because the addition of solubility-enhancing solvents, such as, for example, tetrahydrofuran and methylene chloride, can be dispensed with.

Optimal simple reaction procedure irrespective of whether the reaction has to be effected as a batch process or as a continuous process.

Complete avoidance of halogenated solvents and limitation to the toxicologically unobjectionable polar organic solvents, e.g., the preferred methanol, ethanol, n-propanol and isopropanol.

The reaction procedure in accordance with the present invention contradicts the classical school of thought according to which a good yield and high product quality are to be expected only when the educts have passed completely into solution before the product begins to precipitate out. For carotenoids it is all the more surprising, since this class of substance tends to non-stochiometric inclusions and carotenoid byproducts cannot themselves be separated satisfactorily by recrystallization because of the common structural features.

For many commercially important carotenoids the synthetic route is used involving two $C_{15}$-Wittig salts and the $C_{10}$-dial in a double Wittig reaction. Disadvantageous in this route was primarily the insufficient solubility of these components in almost all non-halogenated solvents. The solubility of the $C_{25}$-intermediate in lower alkanols is also low and the products are anyway hardly soluble. It is therefore very surprising that the consequential heterogeneous reaction procedure does not give rise to disadvantages, either in the yield or in the quality of the product.

Having regard to the variety of Wittig reactions which have been described, it is, moreover, very surprising that a standard reaction procedure is so successful for the synthesis of carotenoids of such a variety of structures (from $C_{20}$ to $C_{50}$).

The present invention is illustrated by the following Examples:

EXAMPLE 1

Manufacture of (all-E)-zeaxanthin 32.88 g (95.8%; 2.03 eq.) of [5-(4-hydroxy-2,6,6-trimethyl-1-cyclohexenyl)-3-methyl-2,4-pentadienyl] triphenylphosphonium chloride and 4.92 g (1 eq.) of 2,7-dimethyl-2,4,6-octatrien-1,8-dial ($C_{10}$-dial) in 490 ml of ethanol were placed in a 500 ml four-necked sulphonation flask equipped with an internal thermometer, stirrer and reflux condenser and cooled to −10° C. while stirring. A solution of 3.60 g of sodium hydroxide in 50 ml of ethanol was added dropwise to the resulting yellowish suspension at −10° C. while stirring and subsequently the reaction mixture was stirred at −10° C. for one hour. After heating to about 80° C. internal temperature within 30 minutes the product suspension was heated at reflux temperature during the following 17 hours. Subsequently, it was cooled to 0° C. and stirred for a further 1 hour, and the thus-obtained zeaxanthin was isolated by suction filtration. Then the filter cake was washed well with ethanol and subsequently freed from neutral salt with water.

The crystallizate was dried under reduced pressure for about 16 hours at 100° C./40 mbar (4 kPa).

In this manner there were obtained 16.0 g of crystalline (all-E)-zeaxanthin with a zeaxanthin content of more than 99% according to high pressure liquid chromatography (HPLC). The yield was 93.7% (based on $C_{10}$-dial).

EXAMPLES 2–12

Various additional Wittig reactions, details of which are compiled in the following Table, were carried out analogously to the procedure described in Example 1. The $C_{10}$-dial was used in each example in a batch amount of 30 mmol. The Table contains various abbreviations, the significances of which are given in the legend appearing after the Table (conventional chemical and other familiar terms do not require detailed explanation).

TABLE

| Example No. | Phosphonium salt (P salt) | Eq. P salt | Solvent | Solvent amount in ml | Base in solvent | Base addition: Duration (h); T (° C.) | Subsequent reaction: Duration (h); T (° C.) | Digestion: Duration (h); T (° C.) | Weight yield (%) | Content of all isomers (%) |
|---|---|---|---|---|---|---|---|---|---|---|
| 2 | Zeanyl, Cl⁻ | 2.03 | iPrOH | 240 | NaOMe in MeOH | 0.5; −10 | 5; −10 to 30 | 16; 80 | 94.9 | 100 |
| 3 | Lycopyl, Cl⁻ | 2.23 | EtOH | 277 | NaOEt in EtOH | 2.5; 10 | 1; 22 | 24; 80 | 65.6 | 99.9 |
| 4 | Lycopyl, —OCOCH₃ | 2.23 | iPrOH | 166 | NaOMe in MeOH | 3; 70 | 0.5; 70 | 4; 100 | 83 | 99.9 |
| 5 | Carotenyl, Cl⁻ | 2.20 | EtOH, 97.5% | 408 | NaOH in EtOH | 5; 10 | 1; 22 | 16; 80 | 90 | 98.2 |
| 6 | " | 2.12 | EtOH, 98% | 355 | NaOH in EtOH | 5; 10 | 1; 30 | 4; 80 | 94.3 | 99.5 |
| 7 | Canthenyl, Cl⁻ | 2.28 | MeOH | 160 | NaOH in MeOH | 2.5; 10 | 3.5; 30 | 2; 60 | 88.4 | 96 |
| 8 | Astenyl, Br⁻ | 2.23 | EtOH | 60 | Butylene oxide (initially) | —; 80 | 18; | — | 89.6 | 94.6 |
| 9 | " | 2.27 | MeOH | 400 | NaOH in MeOH | 2.5; −10 | 2; 10 | 16; 20 | 94.9 | 93.1 |
| 10 | " | 2.28 | " | 160 | NaOMe in MeOH | 2.2; −10 | 3; 30 | 2; 60 | 98.2 | 93.5 |
| 11 | " | 2.27 | " | 400 | NaOH in MeOH | 2.5; 0 | 2; 10 | 1; 20 | 92.7 | 89 |
| 12 | C₅-Wittig ester, Cl/Br⁻ (60:40) | 2.20 | EtOH | 290 | NaOEt in EtOH | 0.25; 22 | 12; 22 | 10; 110 | 80.9 | 97.6 |

Legend
Zeanyl: [5-(4-Hydroxy-2,6,6-trimethyl-1-cyclohexenyl)-3-methyl-2,4-pentadienyl]triphenylphosphonium
Lycopyl: [(2E/Z,4E,6E,Z)-3,7,11-Trimethyl-dodeca-2,4,6,10-tetraenyl]triphenylphosphonium
Carotenyl: [(2E,4E)-3-Methyl-5-(2,6,6-trimethyl-1-cyclohexenyl)-2,4-pentadienyl]triphenylphosphonium
Canthenyl: [5-(2,6,6-Trimethyl-3-oxo-1-cyclohexenyl)-3-methyl-2,4-pentadienyl]triphenylphosphonium
Astenyl: [(2E,4E)-5-(4-Hydroxy-2,6,6-trimethyl-3-oxo-1-cyclohexenyl)-3-methyl-2,4-pentadienyl]triphenylphosphonium
C₅-Wittig ester: [(E)-3-Ethoxycarbonyl-but-2-enyl]triphenylphosphonium
MeOH, EtOH, iPrOH: Methanol, ethanol (absolute), isopropanol
NaOMe, NaOEt: Sodium methoxide, sodium ethoxide

EXAMPLE 13

Manufacture of (R)-3-hydroxy-8'-apo-β-caroten-8'-oic acid ethyl ester

Moist (R)-3-hydroxy-12'-apo-β-caroten-12'-al (calculated dry weight 32.86 g; 0.0896 mol) was suspended in 200 ml of isopropanol in a 1 l swan-necked suction flask equipped with a thermometer, stirrer and argon gasification. 57.13 g (0.1345 mol) of [(E)-3-ethoxycarbonyl-but-2-enyl]triphenylphosphonium chloride and 7.26 g (0.1345 mol) of sodium methylate were added via a funnel through the frit while stirring and gassing with argon, and 220 ml of isopropanol were rinsed in, which gave a dark red suspension. Subsequently, the reaction mixture was heated to an internal temperature of about 50° C. with an oil bath at 55° C. and stirred for about 2¾ hours while monitoring the reaction by thin-layer chromatography (TLC). For the working up, a mixture of 411 ml of water and 384 ml of acetic acid was added and the dark red suspension which had then formed was heated to reflux temperature at an oil bath temperature of 100° C. The suspension was stirred at this temperature for about a further 80 minutes. The suspension was then cooled to room temperature and stirred for a further one hour.

For the isolation of the crude product, the suspension was suction filtered in the swan-necked suction filter flask and the filter cake was washed with aqueous isopropanol (1:1 mixture).

For the isomerization of the product, the filter cake was suspended in 500 ml of water in the swan necked suction filter flask under a weak stream of nitrogen (through the frit). The mixture was heated to reflux temperature with an oil bath heated to 125° C. 50 ml of solvent were distilled off over a stepped condenser within 30 minutes, with the internal temperature increasing from 85° to 98° C. Subsequently, the condenser was again fitted as a reflux condenser and the mixture was stirred vigorously at 98° C. internal temperature in order to suppress the strong foam formation. After 16 hours at the reflux temperature the mixture was cooled to room temperature, suction filtered in the swan-necked suction filter flask and washed with water. Subsequently, the resulting crystals were washed with acetone at −20° C.

For the purification, the filter cake was suspended in 850 ml of acetone in the swan-necked suction filter flask and dissolved at reflux temperature to give an almost clear solution. After removal of the oil bath the mixture was cooled while stirring and without active cooling. Glistening crystals crystallized out at about 45° C. Then the mixture was cooled, stirred at 0° C. for 3 hours, suction filtered and washed twice with 50 ml each time of acetone at −20° C. The crystallizate was dried at 50° C. for about 6 hours in a vacuum drying oven. In this manner there were obtained 26.91 g of the desired product as wine-red, glistening crystals. This corresponded to a 63% yield based on (R)-3-hydroxy-12'-apo-β-caroten-12'-al. The purity was 98.2% according to HPLC.

EXAMPLE 14

Manufacture of β-apo-4'-carotenal

For the manufacture of the dimethyl acetal of [(E)-3-formyl-but-2-enyl]triphenylphosphonium chloride, 72.73 g (0.1891 mol) of this phosphonium salt were placed in a 500 ml round flask equipped with a magnetic stirrer and argon gasification and treated with 100 ml of methanol. 22.7 ml (0.2080 mol) of methyl orthoformate as well as a 4.59% solution of 3.55 ml of p-toluenesulphonic acid in methanol (0.0009 mol of acid) were added thereto at about 25° C. while stirring. The mixture was stirred at 25° C., whereby the crystals rapidly passed into solution. The dark brown reaction solution was stirred for a further hour, then made alkaline with 0.41 ml of 28.82% sodium methylate solution (containing 0.0022 mol of base).

For the performance of the Wittig reaction, 75 g (0.18 mol) of β-apo-8'-carotenal were placed in a 2.5 l sulphonation flask equipped with a stirrer, condenser, thermometer, automatic dosage device (Dosimat) and argon gasification. The β-apo-8'-carotenal was then suspended in 900 ml of dry isopropanol and the resulting red, not very thick suspension was heated to 70° C. The freshly prepared alkaline acetal solution from the previously process step was then added and rinsed in with 100 ml of dry isopropanol. 38.99 ml of sodium methylate solution (containing 0.2080 mol of base) were subsequently dosed in within 30 minutes using the Dosimat. Subsequently, the mixture was stirred at 70° C. for a further hour and thereafter 342.3 mol of 0.5N sulphuric acid (0.0858 mol of acid) were dosed in at 70° C. within one hour using the Dosimat. Then the oil bath was replaced by a water bath, 342.3 ml of 0.5N sodium hydroxide solution (0.1711 mol of base) were added within 15 minutes using the Dosimat and thereby the reaction mixture was cooled to 25° C. The red-brown crystal slurry was stirred for a further 60 minutes, thereafter filtered over a slotted glass suction filter having a paper filter and the filter cake was washed in sequence twice with 340 ml each time of isopropanol and three times with 340 ml each time of deionized water. The thus-obtained wine-red crystals were subsequently dried for 2 days at 50° C. in a vacuum drying oven at 20–30 mbar (2–3 kPa). There were obtained 82.7 g of a cystallizate of the desired product, β-apo-4'-carotenal. The weight yield was 95.2% based on β-apo-8'-carotenal used. The composition of the product according to HPLC or, respectively, Karl-Fischer titration was as follows:

(all-E) Isomer: 94.7%

(Z) Isomer: 1.5%

Residual β-apo-8'-carotenal: 0.2%

Water: 0.2%

EXAMPLE 15

Manufacture of torularhodin aldehyde

For the manufacture of the dimethyl acetal of [(E)-3-formyl-2-butenyl]triphenylphosphonium chloride, 43.93 g (0.1151 mol) of this phosphonium salt were placed in a 250 ml round flask equipped with a magnetic stirrer and argon gasification and treated with 66 ml of methanol. 13.8 ml (0.1266 mol) of methyl orthoformate as well as a 4.59% solution of 2.39 ml of p-toluenesulphonic acid in methanol (0.0006 mol of acid) were added thereto at about 25° C. while stirring. The mixture was stirred at 25° C., whereby the crystals passed rapidly into solution. The dark brown reaction solution was stirred for a further hour, then made alkaline with 0.32 ml of 29.37% sodium methylate solution (0.0017 mol of base).

For the performance of the Wittig reaction, 50.00 g (0.1036 mol) of β-apo-4'-carotenal were placed in a 2.5 l sulphonation flask equipped with a stirrer, condenser, thermometer, automatic dosage device (Dosimat) and argon gasification. The β-apo-4'-carotenal was then suspended in 650 ml of dry isopropanol and the suspension was heated to 65° C., whereby glistening, red-brown crystals formed. The freshly prepared alkaline acetal solution from the previous process step was then added and rinsed in with 100 ml of dry isopropanol. 23.29 ml of sodium methylate solution (0.1266 mol of base) were dosed in within 30 minutes using the Dosimat. Subsequently, the somewhat viscous reaction mixture was stirred at 65° C. for a further 2 hours and thereafter 250 ml of 0.5N sulphuric acid (0.0625 mol of acid) were dosed in using the Dosimat within one hour at 65° C. The crystal slurry thereby became viscous and dark brown. The oil bath was replaced by a water bath, 250 ml of 0.5N sodium hydroxide solution (0.1250 mol of base) were added within 20 minutes using the Dosimat and thereby the reaction mixture was cooled to 20–25° C. The crystal slurry was stirred for 40 minutes, filtered over a slotted glass suction filter having a paper filter and washed twice with 250 ml each time of isopropanol. There were obtained moist, black-brown crystals.

For the purification, the moist crystallizate was placed in a 1.5 l sulphonation flask equipped with a stirrer, reflux condenser, thermometer and argon gasification and treated with 750 ml of isopropanol. The mixture was heated to reflux temperature (83° C.) with an oil bath while stirring. The crystal slurry was stirred at the reflux temperature for one hour and then cooled to 25° C. with a water bath and stirred for one hour. Subsequently, the suspension was suction filtered over a slotted glass suction filter having a paper filter and the crystals were washed twice with 250 ml each time of isopropanol and then three times with 250 ml each time of deionized water. The resulting crystallizate was dried in a vacuum drying oven at 50° C. and 20 mbar (2 kPa) for about 16 hours.

In this manner there were obtained 53.84 g of black, glistening crystals of the desired product torularhodin aldehyde. The weight yield was 94.7% based on β-apo-4'-carotenal used. The composition of the product according to HPLC or gas chromatography (GC) was as follows:

| | |
|---|---|
| (all-E)-Torularhodin aldehyde | 96.8% |
| (Z)-Torularhodin aldehyde | 0.9% |
| Residual β-apo-4'-carotenal | 0.2% |

EXAMPLE 16

Manufacture of crocetin diethyl ester 16.45 g (100 mmol) of 2,7-dimethyl-2,4,6-octatriene-1,8-dial and 93.5 g (220 mmol) of [3-ethoxycarbonyl-but-2-enyl]triphenylphosphonium chloride were suspended in 750 ml of absolute ethanol in a 2.5 l four-necked flask equipped with a mechanical stirrer, thermometer, dropping funnel and nitrogen gasification. 220 ml (220 mmol) of a sodium ethylate solution (1.0M in ethanol) was added dropwise thereto at room temperature while stirring intensively. The reaction mixture was then stirred at room temperature under nitrogen gasification for about 12 hours.

The resulting red suspension was treated with about 2 ml of concentrated acetic acid. Subsequently, 370 ml of ethanol were distilled off from the reaction with an oil bath at 100–110° C. and then 400 ml of water having a low ion content were added. The suspension was then stirred at reflux (internal temperature 82° C.) for a further 10 hours and subsequently stirred for 2 hours in an ice bath (internal temperature 3–4° C.). The precipitate was separated on a glass suction filter and washed with aqueous, ice-cooled ethanol (60% in water). After drying in a water-jet vacuum for about 16 hours at 50° C. there were obtained 34 g of crocetin diethyl ester in red, semi-crystalline, somewhat sticky form (crude product; yield about 88.5% of theory).

The above crude product was suspended in 175 ml of aqueous ethanol (60% in water) and isomerized at 110° C. and at 21 bar (2.1 kPa) pressure under nitrogen gasification for 10 hours. The crystalline product was filtered off under suction in a water-jet vacuum and washed as previously with aqueous ethanol. After drying in a water-jet vacuum for about 16 hours at 50° C. there were obtained 31.1 g of crocetin diethyl ester as a red crystallizate, m.p. 208–209° C.

Yield 80.9% of theory;

HPLC: 90.4% (all-E) isomer;

UV ($E_1^1$): 3052 cm$^{-1}$ (max. at 433 nm).

EXAMPLE 17

Manufacture of diapo-4,4'-carotenedial

For the manufacture of the dimethyl acetal of [7-formyl-3,7-dimethyl-octa-2,4,6-trienyl]triphenylphosphonium chloride, 45.06 g (0.099 mol) of this phosphonium salt were placed under argon gasification in a 2.5 l four-necked sulphonation flask equipped with a stirrer, thermometer, condenser, automatic dosage device (Dosimat) and argon gasification. The contents of the flask were then suspended in 190 ml of methanol and the suspension was treated while stirring at room temperature with 12.94 ml (0.1188 mol) of methyl orthoformate. After the addition of 1.86 ml of a 4.59% solution of p-toluenesulphonic acid in methanol the mixture was stirred at room temperature. The reaction solution thereby remained brown-orange. After the reaction the solution was neutralized with 0.210 ml of a 29.37% solution of sodium methylate (containing 0.0014 mol of base).

For the performance of the Wittig reaction after the acetalization 7.39 g (0.045 mol) of 2,7-dimethyl-2,4,6-octatriene-1,8-dial and 600 ml of isopropanol were added to the above reaction solution at room temperature. An orange suspension was obtained. 20.03 ml of the 29.37% solution of sodium methylate (containing 0.0495 mol of base) were then dosed into this suspension at room temperature within 30 minutes. As a result the temperature rose to about 27° C. and the suspension became dark brown in colour. The reaction mixture was then left to react at room temperature for a further 1.5 hours. The resulting acetal was de-acetalized within 30 minutes with 395 ml of 0.5N sulphuric acid. Thereafter, for neutralization, 395 ml of 0.5N aqueous sodium hydroxide solution were added while stirring. After stirring for about 90 minutes the brown crystal slurry was suction filtered and the filter cake was washed in sequence with isopropanol and deionized water. The resulting black-brown crystals were dried for about 16 hours at 50° C. in a vacuum drying oven at 20–30 mbar (2–3 kPa). In this manner there were obtained in a weight yield of more than 99% 19.26 g of diapo-4,4'-carotenedial as black-brown crystals. The composition of the crude product was about 72% of the (all E) isomer and about 19% of a (Z) isomer according to HPLC.

EXAMPLE 18

Manufacture of β-apo-8'-carotenoic acid ethyl ester 18.83 g (91.3%; 0.04565 mol) of β-apo-10'-carotenal were placed in a 500 ml four-necked sulphonation flask equipped with a stirrer, thermometer, condenser, dropping funnel and argon gasification. 24.16 g (0.0545 mol) of (1-ethoxycarbonylethyl)triphenylphosphonium bromide and 85 ml of ethanol were then added to the contents of the flask with stirring. 74.0 g of a solution of sodium methylate in ethanol (containing 0.054 mol of base) were then added to the resulting red, well-stirrable suspension within 30 minutes. During this addition the temperature rose from 20 to 26° C. and the suspension became viscous. After further reaction at 50° C. for 90 minutes the reaction mixture again became thin. It was treated with 2 ml of acetic acid and then cooled to 17° C. using an ice bath.

The resulting crystals were filtered off under suction and washed twice with 50 ml of ethanol each time at 0° C. After drying the crystals in a vacuum drying oven at 45° C. and 20–30 mbar (2–3 kPa) pressure there were obtained 16.6 g of dark red crystals. This corresponded to a 72.1% yield based on β-apo-10'-carotenal. The content of this crude product of (all E)-β-apo-8'-carotenoic acid ethyl ester was 90% according to HPLC.

EXAMPLE 19

Manufacture of torularhodin 10.0 g (0.024 mol) of β-apo-8'-carotenal were suspended in 130 ml of isopropanol in a 1.5 l four-necked sulphonation flask equipped with a stirrer, thermometer, reflux condenser and argon gasification. The suspension was heated to reflux temperature (about 83° C. at an oil bath temperature of 100° C.). 14.04 g (0.0276 mol) of [7-ethoxycarbonyl-3,7-dimethyl-2,4,6-heptatrienyl]triphenylphosphonium chloride were dissolved in 80 ml of isopropanol and transferred into a 100 ml Hamilton syringe. Then 8.56 g (0.0276 mol) of sodium ethylate in ethanol were drawn into a 20 ml Hamilton syringe. 9 ml of the phosphonium salt solution (10% of the total amount) were added to the pre-prepared suspension of the β-apo-8'-carotenal boiling at the reflux temperature. Thereafter, the remainder of the phosphonium salt solution was dosed in within about 100 minutes and the sodium ethylate solution was simultaneously dosed in within about 2 hours. After completion of the addition the mixture was stirred for a further 30 minutes at the reflux temperature.

Thereafter, the mixture was cooled to 60° C. internal temperature, 150 ml of isopropanol were added and, for the saponification of the torularhodin ethyl ester formed as an intermediate, a solution of 3.75 g (0.0568 mol) of potassium hydroxide in 12.8 ml of deionized water was added. The reaction mixture was then again heated to reflux temperature (80° C.) and left to react for 2 hours. During the saponification the viscosity of the suspension changed such that the stirring speed required appropriate adjustment.

After completion of the saponification 127 ml of 1N sulphuric acid were added thereto and the mixture was stirred for one hour at 80° C. internal temperature. After the subsequent addition of 570 ml of isopropanol the mixture was stirred for 17 hours at 81.5° C. internal temperature and the suspension was then cooled to 20° C. using an ice/water bath. The resulting violet crystals were filtered off under suction and washed in sequence with isopropanol and deionized water.

31.6 g of water-moist crude torularhodin were obtained.

For the purification of the water-moist crude torularhodin, it was digested in sequence in water and in acetone:

The crude torularhodin was suspended in 600 ml of deionized water in a 1 l flask equipped with a stirrer, thermometer, reflux condenser and argon gasification. The suspension was heated using an oil bath at 120° C. to reflux temperature (99° C.) and stirred at this temperature for 2 hours. Thereafter, it was cooled to 20° C. using an ice/water bath and the crystallizate was suction filtered. The resulting crystals were washed with deionized water and subsequently with acetone. There were then obtained 21.7 g of acetone-moist torularhodin. For further purification, the acetone-moist torularhodin was suspended in 600 ml of acetone in a 1.5 l sulphonation flask equipped with a stirrer, thermometer, reflux condenser and argon gasification. The suspension was then heated using an oil bath at 80° C. to reflux temperature (57° C.) and stirred at this temperature for 2 hours. Thereafter, the mixture was cooled to 20° C. using an ice/water bath. The crystals were filtered off under suction and washed with acetone. There were obtained 11.44 g (84.4% yield based on β-apo-8'-carotenal) of torularhodin as violet crystals, the (all-E)-torularhodin content of which amounted to 99.7% according to HPLC.

EXAMPLE 20

Manufacture of β-apo-8'-carotenoic acid ethyl ester 35.16 g of β-apo-12'-carotenal and 54.24 g of [(E)-3-ethoxycarbonyl-but-2-enyl]triphenylphosphonium chloride were suspended in 200 ml of isopropanol. The suspension was warmed to about 30° C. A total of 6.46 g of solid sodium methylate were added thereto within 15 minutes and rinsed in with 15 ml of isopropanol. The reaction was completed by heating to 50° C. within two hours. Subsequently, 215 ml of water were added and the mixture was neutralized with sulphuric acid and isomerized under reflux conditions for 14 hours. Then the mixture was filtered while warm, washed with aqueous isopropanol and dried at 45° C. under reduced pressure (20 mbar, 2 kPa). 43.88 g of β-apo-8'-carotenoic acid ethyl ester were obtained as a crystallizate. This corresponded to a yield of 95.3% based on β-apo-12'-carotenal. The crystallizate content of all isomers of β-apo-8'-carotenoic acid ethyl ester amounted to 98%.

EXAMPLE 21

Manufacture of neurosporaxanthin ethyl ester (β-apo-4'-carotenoic acid ethyl ester)

17.58 g of β-apo-12'-carotenal and 30.53 g of [7-ethoxycarbonyl-3,7-dimethyl-2,4,6-heptatrienyl] triphenylphosphonium chloride were suspended in 400 ml of ethanol in an argon-gassed flask. 23.69 ml of a 18.1% solution of sodium ethylate in ethanol were added while stirring at 0–10° C. within 5 minutes. The subsequent reaction was effected firstly for 30 minutes at 10–15° C. and then for 90 minutes at 25–30° C.

The resulting suspension was treated with 2.5 ml of 1% sulphuric acid and then boiled for 17 hours at the reflux temperature (bath temperature 95° C., internal temperature 76° C.).

The resulting dark red suspension was cooled and the crystals were filtered off under suction and washed successively six times with 40 ml of ethanol/water (1:1) each time at 50° C. and twice with 40 ml of ethanol each time at 25° C. The violet-red crystals were then dried at 45° C. and 20–30 mbar (2–3 kPa) pressure in a vacuum drying oven for about 16 hours.

In this manner there were obtained 21.2 g of neurosporaxanthin ethyl ester, which corresponded to a yield of 80.3% based on β-apo-12'-carotenal. The crystallizate content of (all-E)-neurosporaxanthin ethyl ester amounted to 99.8%.

What is claimed is:

1. A process for the manufacture of a carotenoid intermediate or carotenoid comprising reacting a dispersion of a symmetrical dialdehyde and two equivalents of a triarylphosphonium salt in a polar reaction medium in one step without isolation of the intermediate, wherein less than about 10% by weight of the reactants and a carotenoid intermediate or carotenoid is dissolved in the reaction medium during the reaction process, which is at all times substantially heterogeneous.

2. The process of claim 1, wherein the polar reaction medium comprises a polar organic solvent, remains monophasic on the addition of water in an amount up to about 30 vol. %, and dissolves triarylphosphine oxide which is formed during said reaction.

3. The process of claim 2 wherein the polar organic solvent is a lower alkanol or acetone.

4. The process of claim 3 wherein the polar reaction medium further comprises a polar ester, methyl ethyl ketone, tert.butyl methyl ether or dimethylformamide, or a mixture of one or more of these solvents.

5. The process of claim 4 wherein the polar ester is the methyl or ethyl ester of formic acid, acetic acid or carbonic acid.

6. The process according to claim 3 wherein the polar organic solvent is methanol, ethanol, n-propanol or isopropanol.

7. The process of claim 6 wherein the triarylphosphonium salt is [5-(4-hydroxy-2,6,6-trimethyl-1-cyclohexenyl)-3-methyl-2,4-pentadienyl]triphenylphosphonium chloride and the carbonyl compound is 2,7-dimethyl-2,4,6-octatriene-1,8-dial ($C_{10}$-dial) whereby zeaxanthin is produced.

8. The process of claim 6 wherein the triarylphosphonium salt is [3,7,11-trimethyl-dodecyl-2,4,6,10-tetraenyl]-triphenylphosphonium chloride or acetate, and the carbonyl compound is $C_{10}$-dial whereby lycopene is produced.

9. The process of claim 8 wherein the triarylphosphonium salt is the (2 E/Z, 4E, 6E,Z) isomer of [3,7,11-trimethyl-dodecyl-2,4,6,10-tetraenyl]-triphenylphosphonium chloride or acetate.

10. The process of claim 6 wherein the triarylphosphonium salt is [3-methyl-5-(2,6,6-trimethyl-1-cyclohexenyl)-2,4-pentadienyl]triphenylphosphonium chloride, and the carbonyl compound is $C_{10}$-dial whereby carotene is produced.

11. The process of claim 10 wherein the triarylphosphonium salt is the (2E,4E) isomer of [3-methyl-5-(2,6,6-trimethyl-1-cyclohexenyl)-2,4-pentadienyl] triphenylphosphonium chloride.

12. The process of claim 6 wherein the triarylphosphonium salt is [5-(2,6,6-trimethyl-3-oxo-1-cyclohexenyl)-3-methyl-2,4-pentadienyl]triphenylphosphonium chloride, and the carbonyl compound is $C_{10}$-dial whereby canthaxanthin is produced.

13. The process of claim 6 wherein the triarylphosphonium salt is [5-(4-hydroxy-2,6,6-trimethyl-3-oxo-1-cyclohexenyl)-3-methyl-2,4-pentadienyl] triphenylphosphonium bromide, and the carbonyl compound is $C_{10}$-dial whereby astaxanthin is produced.

14. The process of claim 13 wherein the triarylphosphonium salt is the (2E,4E) isomer of [5-(4-hydroxy-2,6,6-trimethyl-3-oxo-1-cyclohexenyl)-3-methyl-2,4-pentadienyl]triphenylphosphonium bromide.

15. The process of claim 6 wherein the triarylphosphonium salt is [3-ethoxycarbonyl-but-2-enyl] triphenylphosphonium chloride or bromide, and the carbonyl compound is $C_{10}$-dial whereby crocetin diethyl ester is produced.

16. The process of claim 15 wherein the triarylphosphonium salt is the (E) isomer of [3-ethoxycarbonyl-but-2-enyl] triphenylphosphonium chloride or bromide.

17. The process of claim 6 wherein the triarylphosphonium salt is the dimethyl acetal of [7-formyl-3,7-dimethyl-octa-2,4,6-trienyl]triphenylphosphonium chloride, and the carbonyl compound is $C_{10}$-dial whereby diapo-4,4'-carotenedial is produced.

18. The process of claim 6 wherein less than about 2% by weight of the reactants and the produced carotenoid intermediate or carotenoid is dissolved in the polar reaction medium during said reaction.

19. The process of claim 18 wherein the triarylphosphonium salt is [5-(4-hydroxy-2,6,6-trimethyl-1-cyclohexenyl)-3-methyl-2,4-pentadienyl]triphenylphosphonium chloride and the carbonyl compound is 2,7-dimethyl-2,4,6-octatriene-1,8-dial ($C_{10}$-dial) whereby zeaxanthin is produced.

20. The process of claim 18 wherein the triarylphosphonium salt is [3,7,11-trimethyl-dodecyl-2,4,6,10-tetraenyl]-triphenylphosphonium chloride or acetate, and the carbonyl compound is $C_{10}$-dial whereby lycopene is produced.

21. The process of claim 20 wherein the triarylphosphonium salt is the (2 E/Z, 4E, 6E,Z) isomer of [3,7,11-trimethyl-dodecyl-2,4,6,10-tetraenyl]-triphenylphosphonium chloride or acetate.

22. The process of claim 18 wherein the triarylphosphonium salt is [3-methyl-5-(2,6,6-trimethyl-1-cyclohexenyl)-2,4-pentadienyl]triphenylphosphonium chloride, and the carbonyl compound is $C_{10}$-dial whereby carotene is produced.

23. The process of claim 22 wherein the triarylphosphonium salt is the (2E,4E) isomer of [3-methyl-5-(2,6,6-trimethyl-1-cyclohexenyl)-2,4-pentadienyl] triphenylphosphonium chloride.

24. The process of claim 18 wherein the triarylphosphonium salt is [5-(2,6,6-trimethyl-3-oxo-1-cyclohexenyl)-3-methyl-2,4-pentadienyl]triphenylphosphonium chloride, and the carbonyl compound $C_{10}$-dial whereby canthaxanthin is produced.

25. The process of claim 18 wherein the triarylphosphonium salt is [5-(4-hydroxy-2,6,6-trimethyl-3-oxo-1-cyclohexenyl)-3-methyl-2,4-pentadienyl] triphenylphosphonium bromide, and the carbonyl compound is $C_{10}$-dial whereby astaxanthin is produced.

26. The process of claim 25 wherein the triarylphosphonium salt is the (2E,4E) isomer of [5-(4-hydroxy-2,6,6-trimethyl-3-oxo-1-cyclohexenyl)-3-methyl-2,4-pentadienyl]triphenylphosphonium bromide.

27. The process of claim 18 wherein the triarylphosphonium salt is [3-ethoxycarbonyl-but-2-enyl] triphenylphosphonium chloride or bromide, and the carbonyl compound is $C_{10}$-dial whereby crocetin diethyl ester is produced.

28. The process of claim 27 wherein the triarylphosphonium salt is the (E) isomer of [3-ethoxycarbonyl-but-2-enyl] triphenylphosphonium chloride or bromide.

29. The process of claim 18 wherein the triarylphosphonium salt is the dimethyl acetal of [7-formyl-3,7-dimethyl-octa-2,4,6-trienyl]triphenylphosphonium chloride, and the carbonyl compound is $C_{10}$-dial whereby diapo-4,4'-carotenedial is produced.

* * * * *